United States Patent
Igarashi et al.

(10) Patent No.: US 7,859,562 B2
(45) Date of Patent: Dec. 28, 2010

(54) VISUAL AID DISPLAY APPARATUS

(75) Inventors: Takashi Igarashi, Hachioji (JP); Tomoaki Tamura, Hachioji (JP); Hideaki Haraga, Hachioji (JP); Shinri Tanaka, Saitama (JP); Haruhiko Yoshimeki, Machida (JP)

(73) Assignee: Konica Minolta Photo Imaging, Inc., Tokyo (JP)

(*) Notice: Subject to any disclaimer, the term of this patent is extended or adjusted under 35 U.S.C. 154(b) by 1447 days.

(21) Appl. No.: 11/038,350

(22) Filed: Jan. 19, 2005

(65) Prior Publication Data

US 2005/0168569 A1 Aug. 4, 2005

(30) Foreign Application Priority Data

Jan. 29, 2004 (JP) ............... 2004-022311
Mar. 30, 2004 (JP) ............... 2004-098622

(51) Int. Cl.
*H04N 7/18* (2006.01)
(52) U.S. Cl. ............... 348/61; 348/62; 348/63
(58) Field of Classification Search ......... 348/55–80, 348/142–160
See application file for complete search history.

(56) References Cited

U.S. PATENT DOCUMENTS

| | | | | |
|---|---|---|---|---|
| 4,516,157 A | * | 5/1985 | Campbell | 348/158 |
| 4,786,966 A | * | 11/1988 | Hanson et al. | 348/158 |
| 5,060,062 A | * | 10/1991 | Dotson | 348/62 |
| 5,252,997 A | * | 10/1993 | Christenbery | 351/49 |
| 5,471,679 A | * | 12/1995 | Paoluccio | 2/9 |
| 5,777,715 A | * | 7/1998 | Kruegle et al. | 351/158 |
| 6,299,304 B1 | * | 10/2001 | Demuth | 351/41 |
| 6,972,903 B2 | * | 12/2005 | Hara et al. | 359/482 |

FOREIGN PATENT DOCUMENTS

| | | |
|---|---|---|
| JP | 04022358 | 1/1992 |
| JP | 04023579 | 1/1992 |
| JP | 7288754 | 10/1995 |
| JP | 9192164 | 7/1997 |
| JP | 10301055 | 11/1998 |
| JP | 2002156600 | 5/2002 |
| JP | 2002306553 | 10/2002 |
| JP | 200346903 | 2/2003 |

* cited by examiner

*Primary Examiner*—Andy S Rao
(74) *Attorney, Agent, or Firm*—Lucas & Mercanti, LLP

(57) ABSTRACT

A visual aid display apparatus 1 includes, an image capturing section 50 for image capturing of a subject; an image processing section 60 for processing the image, information obtained from the image capturing section 50 so that the image information can be displayed, a display device for displaying the video of image information having been subjected to processing, an ocular optical system for providing video by leading to the eye the light coming from the display device, and a control section 70 for providing control in such a way that the video of the image information having been subjected to image processing can be displayed on the display area of the display section 10. The video of the external world and the image-processed image of the display area A can be viewed simultaneously by an observer on the display section 10.

13 Claims, 19 Drawing Sheets

FREQUENCY CORRECTION

VISUAL AID DISPLAY APPARATUS

TECHNICAL FIELD

The present invention relates to a visual aid display apparatus.

BACKGROUND

Visual disabilities are caused, for example, by cataract, glaucoma, macular degeneration and night blindness. No effective method for medical treatment is available at present for a visually impaired patient having a trouble in the daily life.

A head-mounted display apparatus is proposed as a visual aid display apparatus used by a patient of night blindness, (e.g. Japanese Patent Application Laid-Open No. 7-288754 publication), and amblyomia spectacles or the like are also proposed as a visual aid display apparatus used by a patient of amblyomia (e.g. Japanese Patent Application Laid-Open No. 9-192164 publication).

An apparatus disclosed in the Japanese Patent Application Laid-Open No. 2002-156600 publication is known as a visual display apparatus worn on the face. However, this disclosure fails to propose a technological concept of displaying by compressing the luminance of an inputted image, reducing the luminous intensity or processing the image information captured by an image-capturing apparatus.

The prior art visual aid display apparatus has been designed in a large-sized goggle type that covers the entire face of a patient. This is not very convenient for a patient in leading the daily life. Thus, the problem with this prior art is that a landscape cannot be identified and the observer's eyes cannot be checked by a person providing medical treatment. Further, wearing a prominent apparatus in the daily life will produce a sense of incompatibility with the surrounding.

To assist a visually handicapped person to walk, a proposal has been made of a method wherein an image captured by a TV camera is displayed on a portable CTR. However, this requires assistance of another person carrying a TV camera, and also requires the handicapped person to hold the CRT, with the result that both hands are occupied.

In the prior art, the eye protector used for reducing the sun dazzle of the user absorbs a specific wavelength of e.g. 500 nm or less, and is effective in reducing the dazzle of light to a certain extent. However, since the information of a specific wavelength is completely lost, the color of signals and others cannot be easily identified. This is a problem in the prior art. Further, when sunglasses are worn, it is necessary to prepare many types of glasses having different transmittances and to select an appropriate type in conformity to a particular environment such as outdoors and indoors. The problems are also found in the higher costs in preparing a plurality of glasses and the trouble of having to carry a plurality of glasses and to use them in conformity to the particular environmental requirement.

SUMMARY

The present invention is to provide a visual aid display apparatus capable of providing a visual aid display, without sacrificing the image information in a specific wavelength area, thereby assisting a visually handicapped observer to identify the external information whenever required, with the result that comfortable activities of daily living are ensured.

To solve a problem and to achieve an object, the present invention has the following configuration.

The present invention comprises, an image capturing section for capturing a subject, an image processing section for performing processing so as to display the image information obtained from the image capturing section, a display section further comprises a display device for displaying the video of the image information having been processed by the processing section, and an ocular optical system for providing video by leading the light from of the display device to the eyes, and a control section for providing control in such a way that the video of the image information subjected to image processing can be displayed in the display area of the display section, wherein the video of the external world and image-processed image in the display area are visible concurrently to the observer on the display section.

The display area is characterized in that the size in the vertical direction is greater than that in the lateral direction.

The display area is further characterized in that installation site can be changed.

The transmittance in the display area does not exceed 40 percent that in the area surrounding the display area.

The control section is characterized in that the information required for display is extracted from the image-capturing visual field of the capturing section, and the size of the display area is changed, based on the image information.

The control section extracts the information required for display, from the image-capturing visual field of the capturing section, and moves the display area, based on the visual field information.

The control section allows an enlarged view to be displayed according to the image characteristic information obtained from the image capturing section.

The image processing section carries out image processing, including enlargement/reduction processing, frequency correction, color tone correction, luminance compression and image extraction.

The present invention further comprises a warning means for detecting approach to the subject and issuing a warning.

The present invention provides a visual aid display apparatus comprises a display section for a displaying video, an ocular optical system, and a transparent plate-formed member for holding the ocular optical system.

This visual aid display apparatus is used with the ocular optical system located before the eyes of an observer and the plate-formed member positioned face to face with the eyes, wherein the light from the display section is led to the eyes through the ocular optical system to provide a virtual image of the video displayed on the display section, and the light of the external world is allowed to pass by to reach the eyes, thereby providing the image of the external world.

This visual aid display apparatus is further characterized in that the luminance ratio of the inputted image information is compressed, and an image is displayed on the display section.

Control is provided in such a way that the brightness on the display section does not exceed 1,000 cd/m$^2$.

The chroma of the inputted image information is increased to display an image on the display section.

The profile of the inputted image information is enhanced to display an image on the display section.

The brightness displayed on the display section is controlled in conformity to a photometer section and the brightness measured by the photometer section.

DESCRIPTION OF THE PREFERRED EMBODIMENT

The following describes the embodiments the visual aid display apparatus according to the present invention, without the present invention being restricted thereto. The embodiments of the present invention indicate the best ones according to the present invention, without terminologies being restricted thereto.

Figure 1:
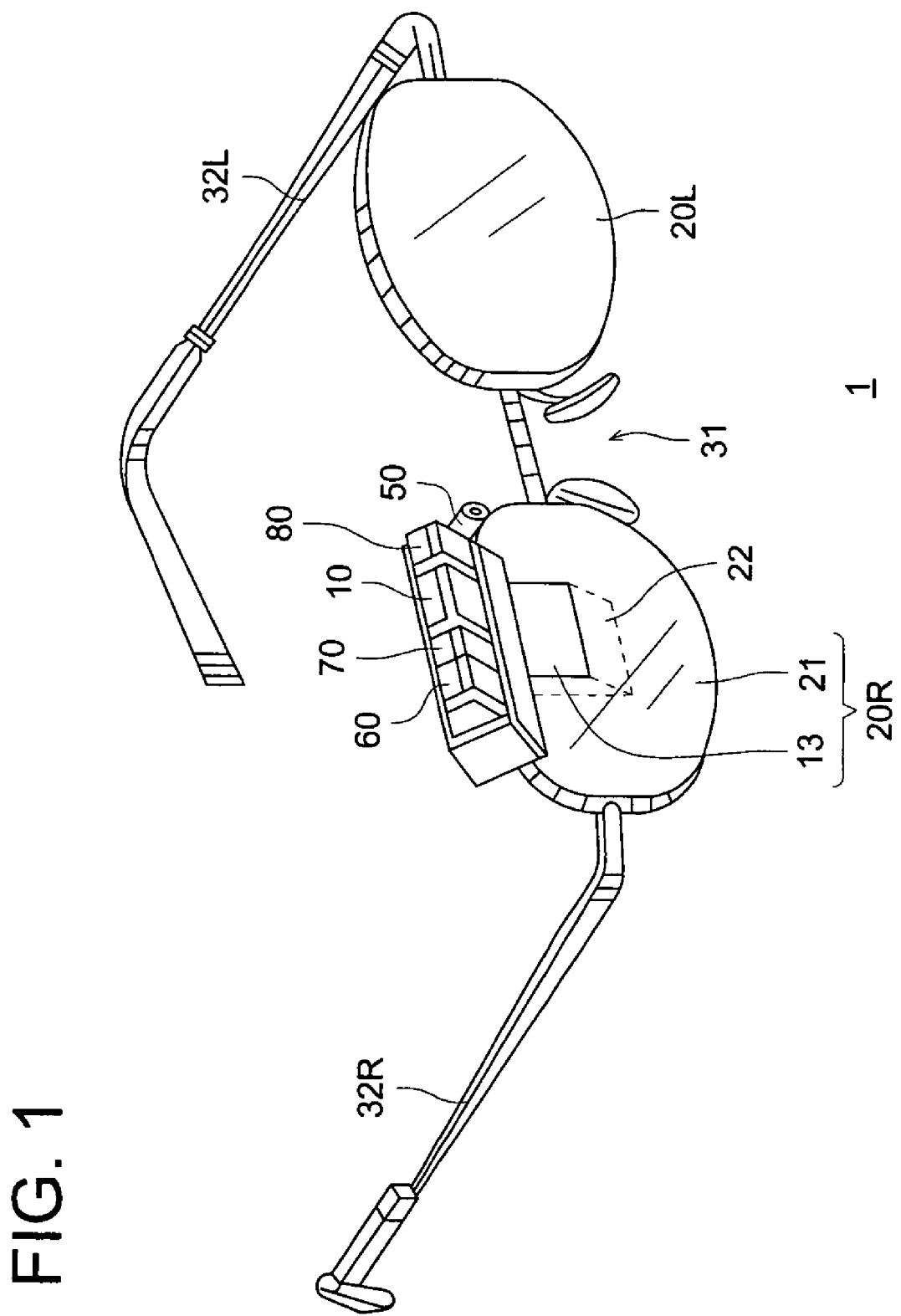
FIG. 1 is a drawing showing the external appearance of a visual aid display apparatus.

FIG. 1 is a drawing showing the external appearance of a visual aid display apparatus. The visual aid display apparatus 1 of this embodiment comprises a display section 10, an image capturing section 50, an image processing section 60, a control section 70, a data input section 80, a pair of right/left prisms 20L and 20R, a nose pad 31 and a pair of right/left temples 32L and 32R. It is worn on the face of the observer so that the prisms 20L and 20R are located in front of the right and left eyes.

Figure 2:
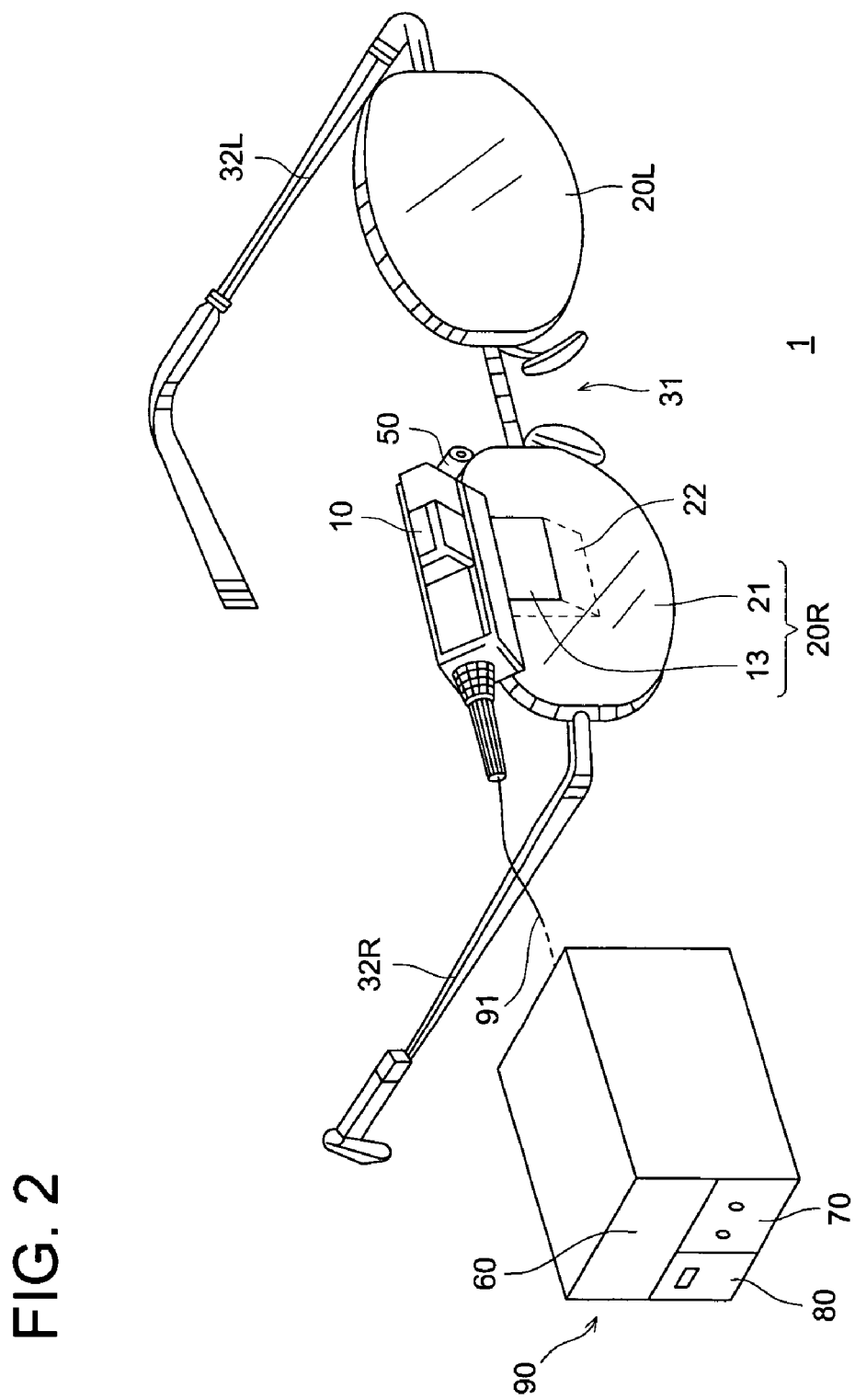
FIG. 2 is a drawing showing the external appearance of the visual aid display apparatus wherein an image processing section, a control section and a data input section are built integrally with a display apparatus unit.

In FIG. 1, the image processing section 60, control section 70 and data input section 80 are mounted together with the display section 10. It is also possible to arrange such a configuration, as shown in FIG. 2, that the image processing section 60, control section 70 and data input section 80 are mounted integrally with an apparatus unit 90, and a cable 91 is used to supply power to the image capturing section 50 and display section 10. The nose pad 31 is mounted on the prisms 20L and 20R so as to connect them together. The temples 32L and 32R are mounted on the ends of the prisms 20L and 20R. When mounted, the nose pad 31 contacts the nose and the temples 32L and 32R contact the ears, and the side and back portion of the head; thus, the visual aid display apparatus 1 is supported by these three points. The temples 32L and 32R are rotatable about the axis in the perpendicular direction (not illustrated) provided in the vicinity of the prisms 20L and 20R. When not used, it can be folded inside.

Figure 3:
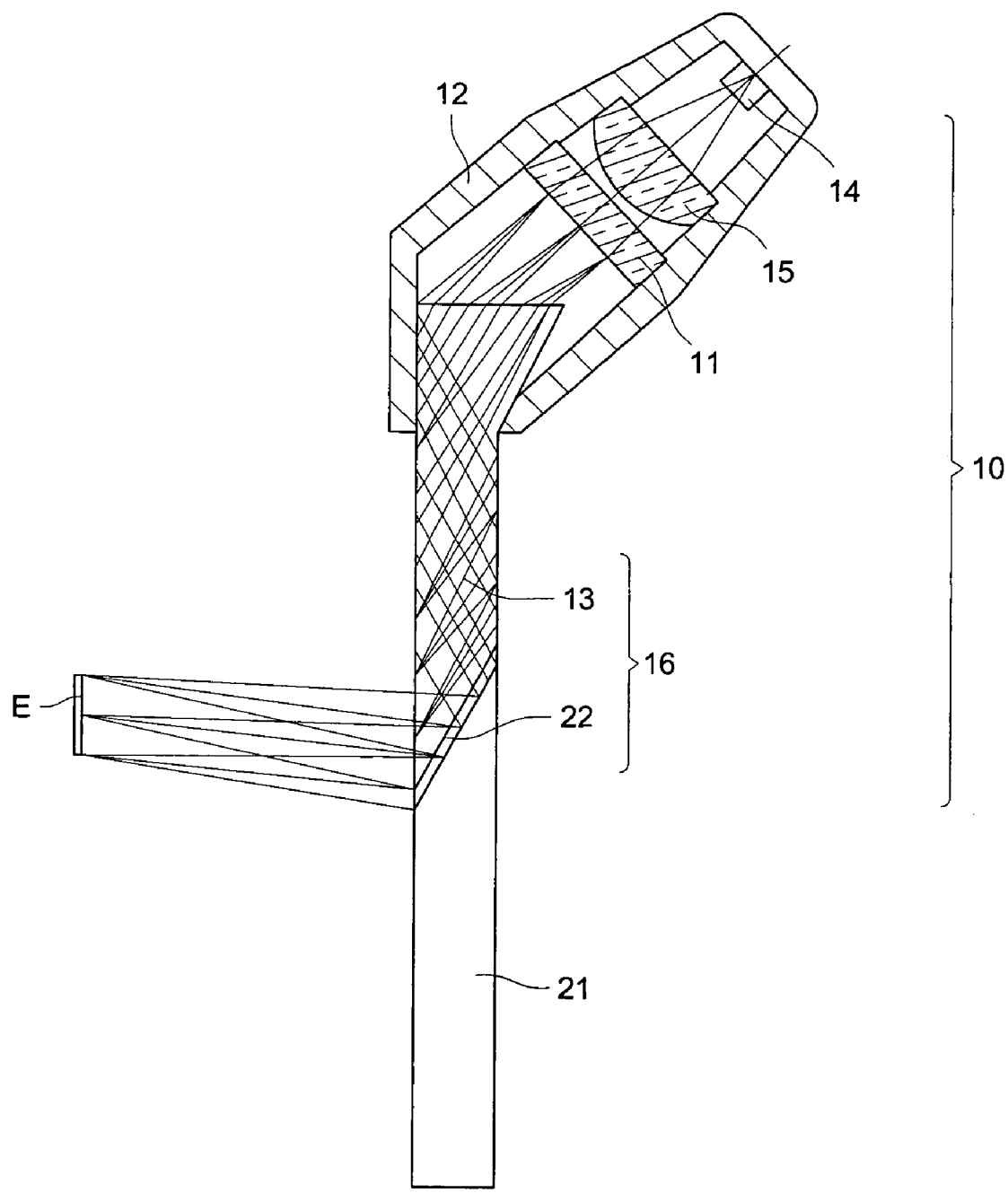
FIG. 3 is a cross sectional view of the visual aid display apparatus including the display section thereof.

The display section 10 is mounted on the prism 20R. FIG. 3 shows the cross section including that of the display section 10. The display section 10 consists of a transmission type LCD (liquid crystal display) 11, a casing 12, a prism 13, a LED (Light-Emitting Diode) 14 and lens 15. The LCD 11 shows the video to be displayed to the observer. The illumination light is modulated by the displayed video. The casing 12 accommodates the LCD 11, LED 14 and lens 15, and holding them in position. The LED 14 is a light source for illuminating the LCD 11. The lens 15 leads the light emitted from the LED 14, uniformly over the entire surface of the LCD 11.

The video or display of the LCD 11 and light emitted from the LED 14 are controlled by the control section 70, and the image information captured by the image capturing section 50 is subjected to image processing by the image processing section 60, whereby electric power and video signal are supplied.

The prism 13 is a flat plate made of transparent glass or resin. The prism 13 leads the light of the LCD 11 to the observer, so that the virtual image of the video displayed on the LCD 11 is displayed. The top end of the prism 13 is formed in a wedge shape where the edge is thicker than the inner portion. The casing 12 is mounted on the prism 13 so as to sandwich this wedge-shaped top end.

The prism 20L is a flat plate made of a single member. The prism 20R is also a flat plate, which is made of a prism 13 and a prism 21—not of a single member. The prism 20L and prism 21 are made of the same material as the prism 13, and these thee parts have no difference in refraction index. The prism 13 and prism 21 constituting the prism 20R are formed in a complementary shape without any clearance in-between, and are formed so that the surfaces are continuous. Except that the prism 13 has a wedge-shaped top end, the prisms 20L and 20R are symmetrical to each other, similarly to commonly used glasses. Thus, an observer wearing the visual aid display apparatus 1 on his or her face views the external world through the prisms 20L and 20R.

The wedge-shaped bottom end of the prism 13 is formed in such a manner that the front surface (surface farther from the eye E) comes closer to the rear surface (surface closer to the eye E), as one goes to the edge. The front surface of this wedge-shaped portion, i.e., the surface in contact with the prism 21 forms a flat plane, on which a hologram 22 is formed. The hologram 22 is located immediately before the eye E, when the apparatus is worn. The prism 13 and hologram 22 constitute an ocular optical system 16.

The prism 13 leads the light of the LCD 11 inside from the end face of the top end. It leads the light to the hologram 22 while completely reflecting it a plurality of times on the front and back surfaces. Diffracting the light having been led inside, the hologram 22 forms a luminous flux close to the parallel beams of light and leads it into the eye E. Then the virtual image of the video displayed on the LCD 11 is shown to the observer. The hologram 22 hardly acts on the light from the external world. The virtual image is observed as being overlapped with the center of the external image.

The visual aid display apparatus 1 leads the light of the LCD-11 to the hologram 22 while allowing the light of the LCD 11 to be reflected inside the prism 13. This arrangement permits the size of the prism 20R to be increased. The bottom end of the prism 13 is formed in a wedge shape. Since it is jointed with the prism 21 made of the same material, there is no reflection of light from the external world passing through the bottom end of the prism 13. Thus, the visual aid display apparatus 1 provides a high-quality image to be displayed, without the external image being contorted at the center or discontinuous.

The LCD 11 has a rectangular form with a greater size in the lateral direction, and one through several strings, each string consisting of more than ten characters, are arranged in the lateral direction. This arrangement allows the observer to get many pieces of information at one time. In the present embodiment, the video is displayed on the right eye. Needless to say, it is also possible to arrange such a configuration that the video is displayed on the left eye.

Figure 4:
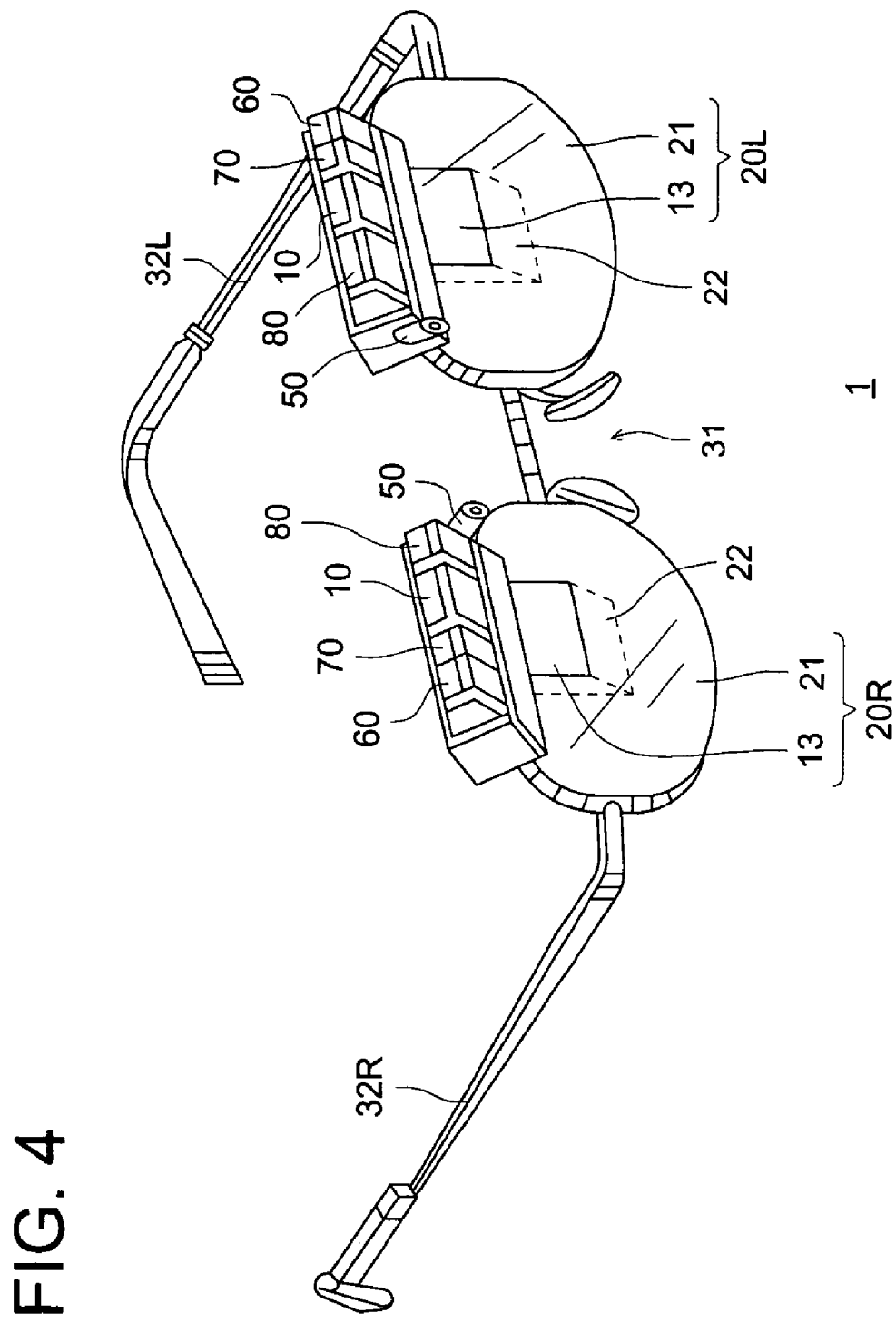
FIG. 4 is a drawing showing the external appearance of the visual aid display apparatus as a second embodiment of the present invention.

FIG. 4 shows the external view of the visual aid display apparatus 1 as a second embodiment according to the present invention. The visual aid display apparatus 1 of this embodiment is provided with a pair of right/left display sections 10L and 10R so that video is displayed on the right and left eyes. At the same time, the prisms 20L and 20R are equipped with the power to allow the visual acuity to be corrected. The configuration of the display sections 10L and 10R is the same as that of the display section 10 of the visual aid display apparatus 1 given in a first embodiment, except that prisms 13L and 13R have a curvature.

The power of the prisms 20L and 20R is set in response to the visual acuity of a user. When the prisms 20L and 20R are provided with negative power, myopia is corrected, and; and when provided with positive power, hyperopia is corrected. The joint surfaces with the prisms 21L and 21R on the bottom ends of the prisms 13L and 13R are formed in a flat shape and the formation of the holograms 22L and 22R is easy.

Figure 5:
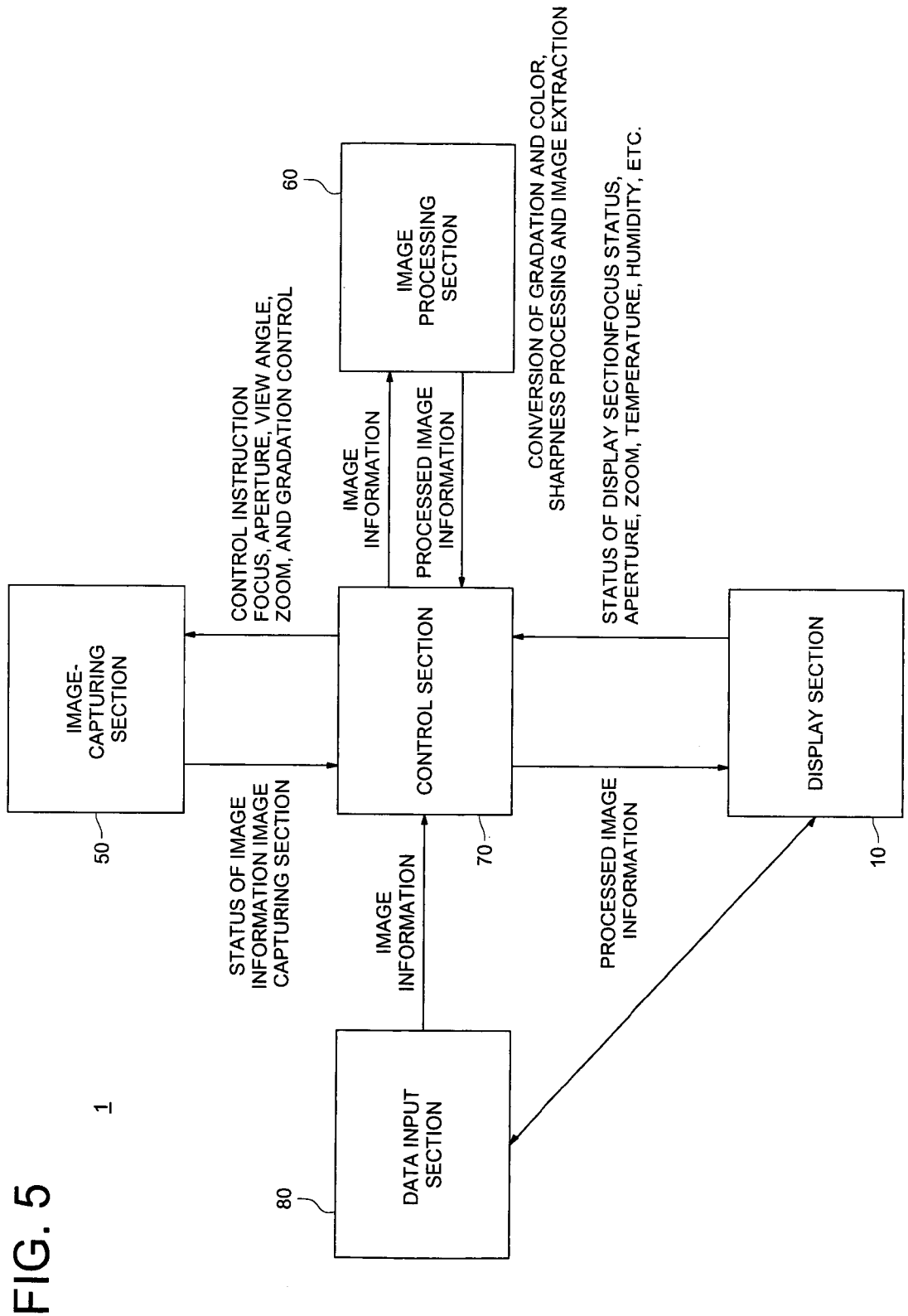
FIG. 5 is a configuration block diagram representing the visual aid display apparatus.
Figure 6:
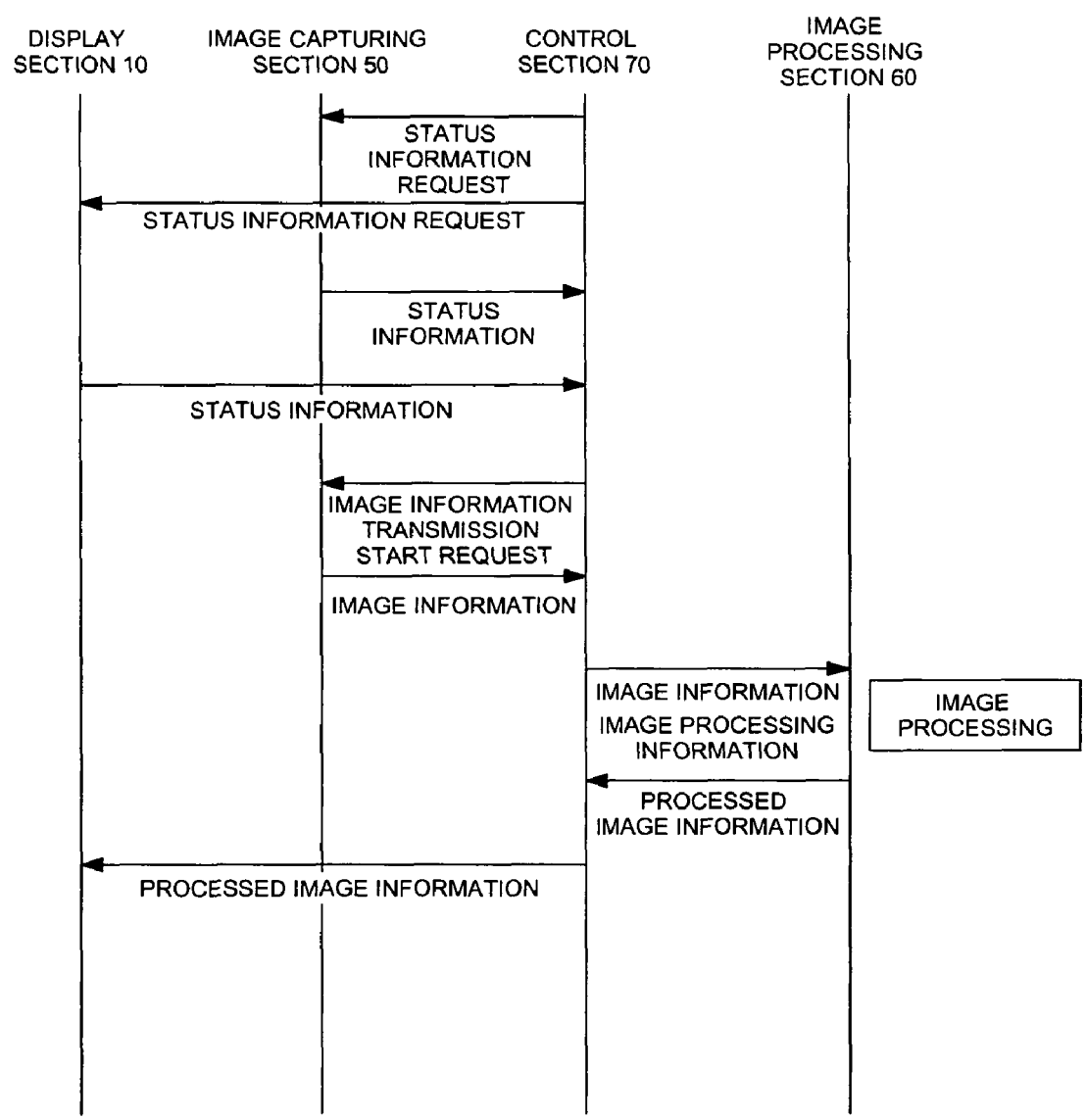
FIG. 6 is a flowchart representing the visual aid display apparatus.
Figure 7:
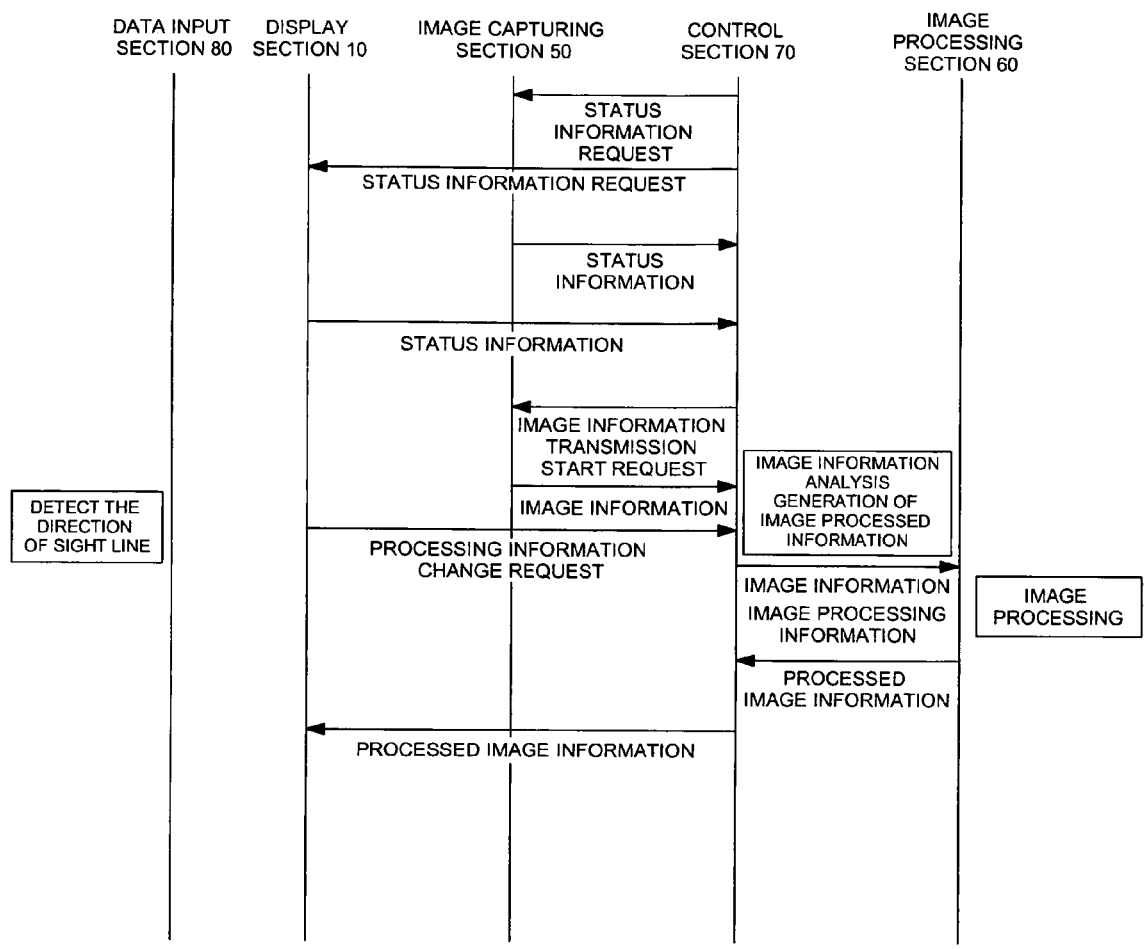
FIG. 7 is a flowchart representing the operation of the visual aid display apparatus for updating the image processing information.

FIGS. 5 through 7 shows the configuration wherein the image information obtained by image capturing operation is displayed on the display section 10 of the visual aid display apparatus 1. FIG. 5 is a configuration block diagram representing the visual aid display apparatus.

The display section 10 is configured as shown in FIGS. 1 through 4. It contains a display device for displaying the video of the image information having been processed, and an ocular optical system for leading lead the light of the display device to the eyes so that a visible image is shown to the observer. In the image capturing section 50, an image is captured using a CCD camera, for example, and focus control, aperture control, field angle control, zoom control and gradation control are provided in response to the control instruction from the control section 70, whereby a subject image is captured. Such control information is sent to the control section 70 whenever required.

The control section 70 includes a CPU in charge of control in general, a ROM for storing a control program, a RAM for temporary storage of data, and a battery. The battery may be configured as a separate unit so that electric power is supplied by a power cable. The battery of the control section 70 provides electric power to the display section 10, image capturing section 50, image processing section 60 and data input section 80. The control section 70 sends the image information obtained from the image captured by the image capturing section 50, to the image processing section 60, and receives the image information having been subjected to image processing by the image processing section 60. The control section 70 receives such environmental conditions as focus status, aperture, zoom, temperature and humidity by means of the stator of the display section 10, and sends the image information having been subjected to image processing, to the display section 10.

The image processing section 60 contains a CPU in charge of processing in general, a ROM for storing a processing program, and a RAM for temporary storage of data, and applies such image processing as gradation conversion, color conversion, sharpness processing and image extraction. As described above, the image processing section 60 provides image processing so that the image information obtained by image capturing can be displayed as video. The data input section 80 is used to input the sight line information and such environmental information as temperature and humidity, and such information is sent to the display section 10 and control section 70. Having received the sight line information and such environmental information as temperature and humidity, the display section 10 sends it to the data input section 80, and the information is sent to the control section 70 from the data input section 80.

FIG. 6 is a flowchart representing the operation of the visual aid display apparatus. This visual aid display apparatus 1 requests the status information to be sent to the image capturing section 50 and display section 10 from the control section 70, and status information request is sent to the control section 70 from the image capturing section 50 and display section 10. Image information transmission start request is send from the control section 70 to the image capturing section 50, and the image information obtained by capturing the image of a subject is sent from the image capturing section 50 to the control section 70.

The control section 70 sends the image information obtained by capturing the image of the subject and the image processing information, to the image processing section 60. Based on the image processing information, the image processing section 60 applies image processing so that it can be displayed as video, and sends the processed image information to the control section 70. In this case, the image processing information conforming to the information of the observer is basically set. This image processing information is used to implement gradation conversion and sharpness enhancement.

The control section 70 sends the image information having been subjected to image processing, to the display section 10. The display section 10 allows both the video of the external world and the image processed image in the display area to be viewed by the observer at the same time.

FIG. 7 is a flowchart representing the operation of the visual aid display apparatus for updating the image processing information. This visual aid display apparatus 1 shows an embodiment wherein the set image processing information is updated. As shown in FIG. 6, the set image processing information basically conforms to the information of the observer, and this set image processing information can be updated. The data input section 80 detects the direction of sight line, and sends processing information updating request to the control section 70. Based on the detected direction of the sight line, the control section 70 analyzes the image information and generates the image processing information, whereby the image processing information is updated.

Based on the updated image processing information, the image processing section 60 performs image processing so that it can be displayed as video, and sends the image information having been subjected to processing, to the control section 70. The conditions for changing this image processing information depends on the environmental changes (brightness, temperature and humidity in the surrounding area), sight line detected by the observer and image information obtained by image capturing.

As shown in FIGS. 8 through 12, the visual aid display apparatus 1 as the present embodiment is worn on the face of the observer, and both the video of the external world and the image processed image in the display area A can be viewed by the observer in the display area A. The video of the image information having been subjected to image processing is displayed in the display area A.

The apparatus is worn on the face of the observer, and the image information obtained by image capturing is subjected to image processing so that it can be displayed as video. The video of the image information having been subjected to image processing is displayed in the display area A for the visual field of an able-bodied person by means of the display section 10. This arrangement allows the view to be closer to the video that can be identified by the observer at normal times. Moreover, both the video of the external world and the image-processed image of the display area A can be viewed by the observer simultaneously on the display section 10. This allows the actual landscape to be identified. Further, the eyes of the observer can be identified by the person giving medical treatment. A person talking face to face with him or her in the daily life can enjoy conversion by viewing the eyes of the observer. Since this apparatus does not have a peculiar shape as in the case of the goggles, it does not give a sense of incompatibility in the daily life when it is worn and used.

Figure 8:
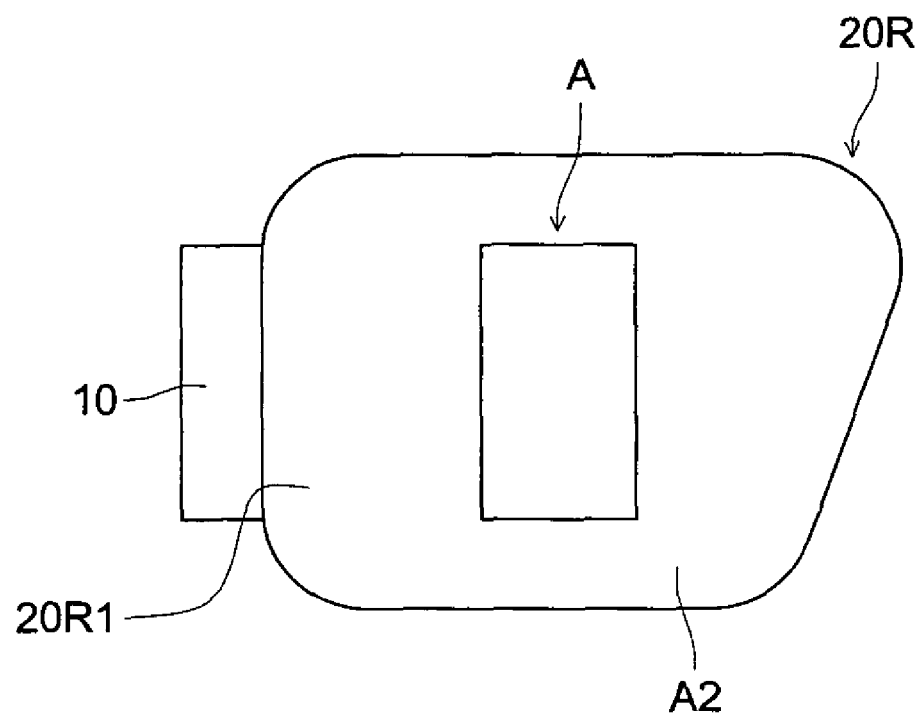
FIG. 8 is a drawing showing a display area of the image processing information.
Figure 9:
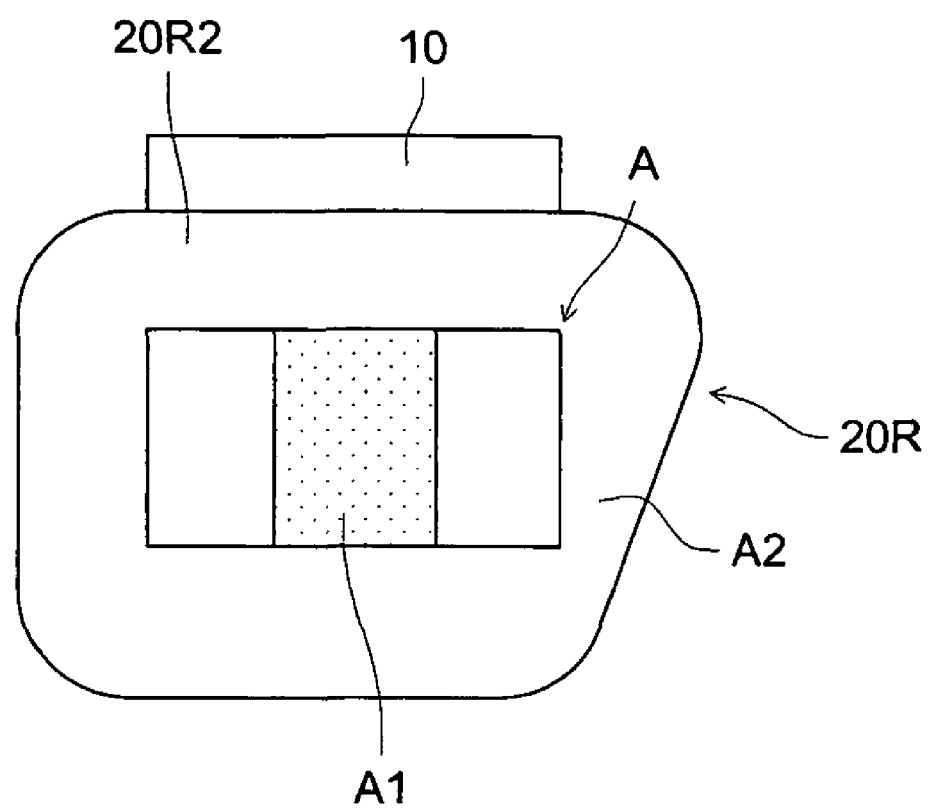
FIG. 9 is a drawing showing another display area of the image processing information.
Figure 10:
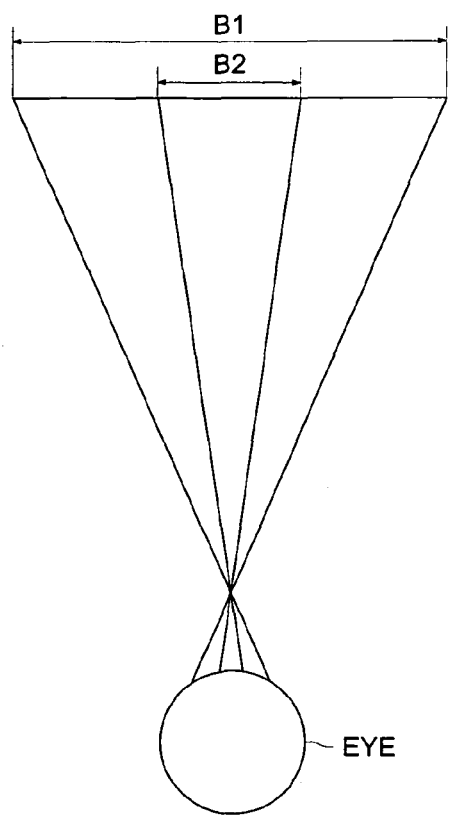
FIG. 10(a) is a drawing showing a display area of the image processing information.
FIG. 10(b) is a drawing showing a display area of the image processing information.
Figure 10:
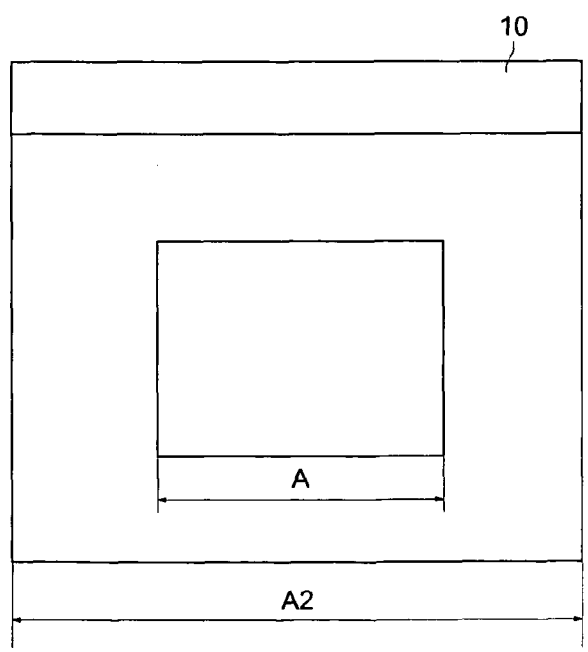

This display area A can be arranged as shown in FIGS. 8 and 9. The display area A shown in FIG. 8 can be set in such a way that, by mounting the display section 10 on the outside portion 20R1 of the prism 20R in the vertical direction, the size in the vertical direction is greater than that in the lateral direction in a rectangular form. As described above, the display area A is set in portrait orientation for easier viewing by the observer, by ensuring the size in the vertical direction is greater than that in the lateral direction.

The display area A shown in FIG. 8 is set in such a way that, by mounting the display section 10 on the top portion 20R2 of the prism 20R in the vertical direction, the size in the lateral direction is greater than that in the vertical direction in a rectangular form. In this case, by masking both sides of the display area A, it is possible to form a display area A1 wherein the size in the longitudinal direction is greater than that in the lateral direction. Without being restricted to a rectangular shape, the display area A can be formed in an elliptical shape. In the elliptical display area A, setting is made in such a way that the size in the longitudinal direction is greater than that in the lateral direction in terms of the ratio of a circumscribed rectangular shape.

The display section 10 can be mounted on either the outside portion 20R1 of the prism 20R shown in FIG. 8 or on the top portion 20R2 of the prism 20R shown in FIG. 9. The mounting position can be changed freely in response to the requirements of the observer. If the prism 20R including the display section 10 is formed in a regular square, the shape of the display area A can be changed to portrait orientation or landscape orientation as required, by turning only the prism 20R 90 degrees.

The transmittance of the display area A does not exceed 40% as compared to that of the area A2 around the display area A. When no image is displayed, the display area A works as a glass ball, and a doctor or the person sitting in front can watch the movement of the eyeballs of the observer, enabling an exacter diagnosis.

To give a specific example of image processing for the display area, when the observer is visually impaired due to contraction of visual field or the like, he or she can view only a limited visual field B2 shown in FIG. 10(a), as compared to the average visual field B1 of the able-bodied people. In such a case, if the display area A shown in FIG. 10(b) is smaller than the visual field B when the observer wears the visual aid display apparatus 1, the observer as a visually impaired person can get the image information of the same level as that of the able-bodied person when the image information of the visual field B1 is displayed in the display area A2. Further, when the visual field B2 is smaller than the display area A processing of reduction is performed in the display area A within the range of being accommodated in the visual field B2, and the information of the visual field B1 is displayed. This procedure allows the observer to get the image information of the same level as that of the able-bodied person.

Further, if a defect of visual field in the display area A occurs to the observer as a visually impaired person (not illustrated), display can be given in the display area A, not the visual field defective area.

Figure 11:
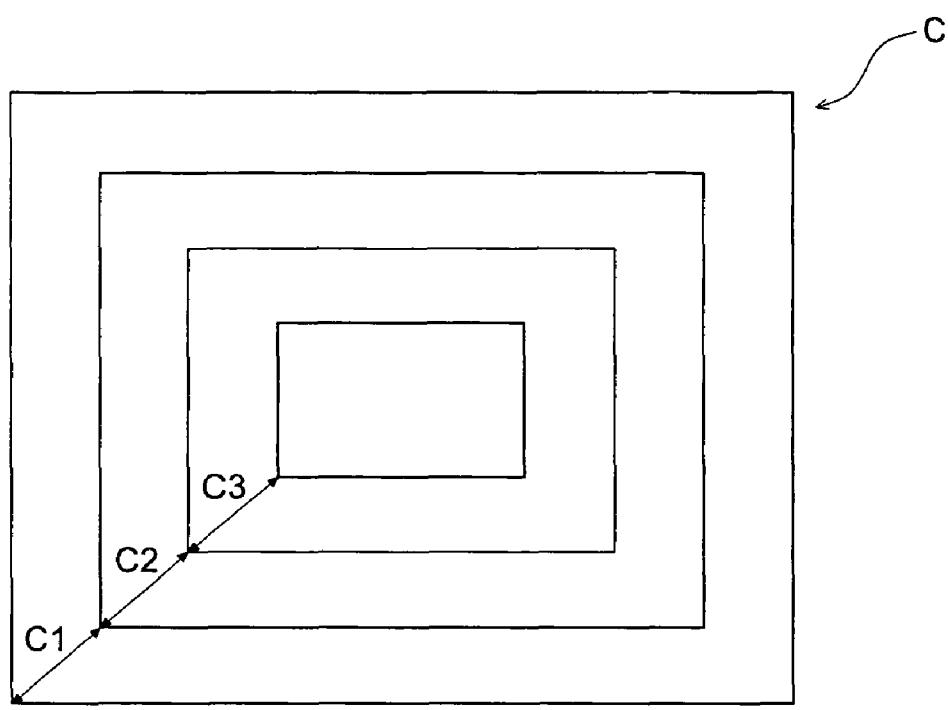
FIG. 11 is a drawing showing another display area.

In the embodiment shown in FIG. 11, the control section 70 extracts the visual field information required for display, from the image-capturing visual field of the image capturing section 50. Based on the image information, processing of image extraction is applied in the image-capturing area—e.g., extraction of C2 and C3 from the C1—so that the image is enlarged for easy viewing. For example, based on the characteristics of the inputted image in the image capturing section 50, a character is automatically recognized. Upon recognition of the character, the mode is automatically switched over to the enlarged projection mode, whereby the size of the image-capturing area C is enlarged. For character recognition is, the white margin is detected from the density of the image obtained by image capturing in the projection/integration section and the image is divided into blocks. The divided blocks are projected and integrated, and are further divided. The aspect ratio (length-to-width ratio) of the block obtained by the repetition of this procedure is calculated. Whether the image is a character image or a photographic image is determined by whether the aspect ratio is greater than a set value or not. Based on the image characteristic information obtained from the image capturing section 50, enlarged display is given, thereby assisting the observer to get easy viewing. It goes without saying that this can be achieved by providing an enlarged display of the image information in the display area A.

Figure 12:
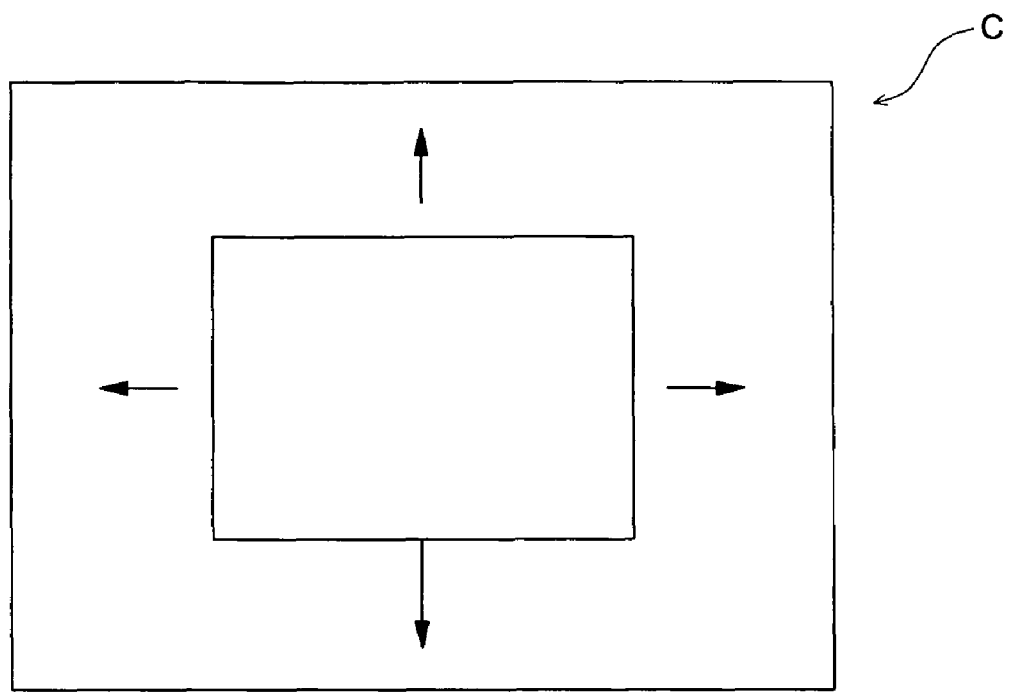
FIG. 12 is a drawing showing a display area.

In the embodiment shown in FIG. 12, the control section 70 extracts the visual field information required for display, from the image-capturing area C of the image-capturing visual field of the image capturing section 50. Based on the visual field information, it moves the image extraction area displayed in the display area A, thereby providing easy viewing. For example, the image-capturing information of a wide-angle lens is displayed inside the specific visual field, and the display area A is moved in conformity to the movement of the eyeballs. The information of the specific site is displayed based on the information of the wide-angle lens. If the angle of field of the observer is smaller than that of the normal person, the information on the angle of field equivalent to that of an average general person can be projected inside the visual field identifiable by the observer.

Figure 13:
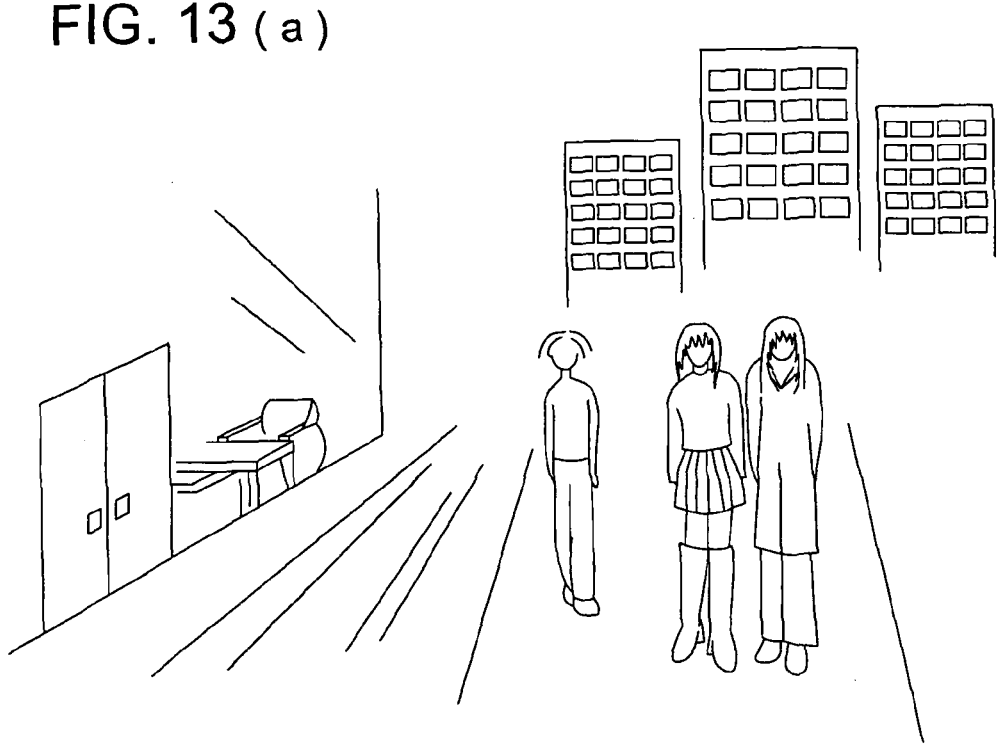
FIG. 13(a) is a drawing showing the display to which image processing of profile enhancement has been applied.
FIG. 13(b) is a drawing showing the display to which image processing of profile enhancement has been applied.
Figure 13:
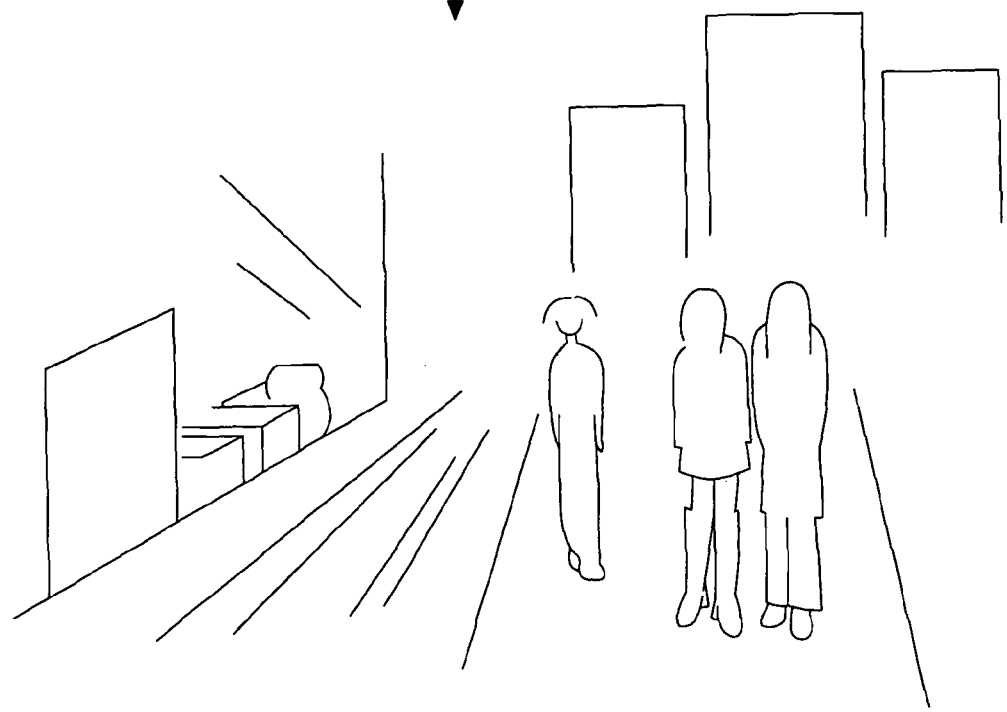

The image processing section 60 performs image processing such as enlargement/reduction processing, frequency correction, color tone correction, luminance compression and image extraction, so that the image information can be displayed as video based on the image processing information, thereby assisting the observer to get easy viewing. For example, in the image processing of frequency correction, profile enhancement makes it easy to capture the profile of an object of the external world, as shown in FIGS. 13(a) and (b). In the image processing of color tone, easy viewing by a visually impaired person such as an achromate can be ensured by display through enhancement of a specific color or by display in a monochromic form. For the person suffering from anomalous trichromatism, the colors that could not be identified are subjected to color conversion on a screen and are displayed in a different density or color on the screen, whereby easy viewing is achieved. Further, in the image processing of luminance compression for a visually impaired observer, easy viewing is provided by reducing the contrast by logarithmic transformation or increasing the overall luminance.

Figure 14:
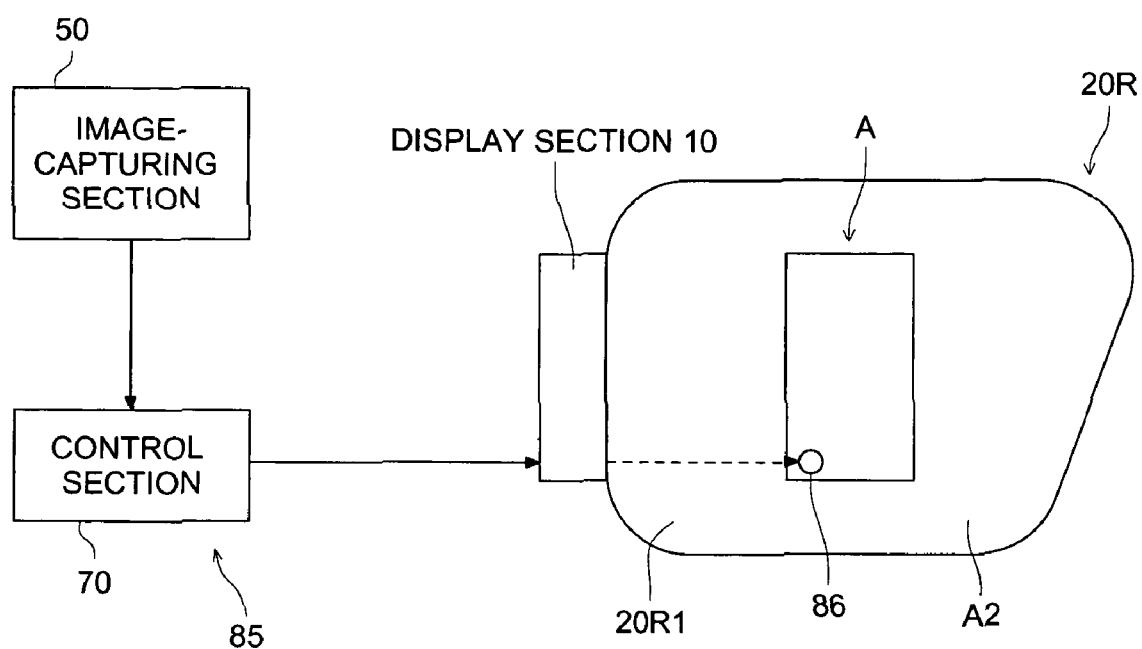
FIG. 14 is a drawing showing a warning means.

Various types of processing, including processing of enlargement or reduction, lightness correction, chroma correction and profile enhancement can be applied to the image captured in the aforementioned manner. At least one of these types of image processing or two or more types in combination can be applied. If image processing of enlargement or reduction is carries out, a distant subject can be viewed as if it were located nearby, or a very large subject that cannot be viewed at one time can be viewed simultaneously. If lightness is corrected, night-vision is enabled, and ensures greater safety in driving during the night. Direct viewing of the sun or the interior of a blast furnace is enabled by image processing of reducing the lightness, without injuring the eyes. Further, for a person suffering from anomalous color vision, processing of color correction is performed. For example, when he or she is unable to differentiate between the red and green, the colors are converted into colors that can be easily distinguished, whereby problems arising from anomalous color vision can be solved. At the same time, for the person suffering from defective visual field, the problems can be solved by changing the image position. When a subject looks blurred due to cataract, processing of profile enhancement is preferred. Further, the visual aid display apparatus 1 of the present embodiment is provided with a warning means 85 for issuing a warning upon detection of approach to a subject, as shown in FIG. 14. This warning means 85 detects the approach to the subject from the image information coming from the image capturing section 50, and the warning mark 86 is displayed on the display area A by the display section 10, whereby the observer is notified of a possible danger. Without being restricted to image information, the warning means 85 can use the focus information, or both the image information and focus information. Without being restricted to the arrangement wherein warning mark 86 is displayed in the display area A, the attached earphones, for example, may be used to issue a warning sound. Alternatively, it is also possible to arrange such a configuration that the display by the display section 10 is suspended to give a warning.

Embodiment 3

Figure 15:
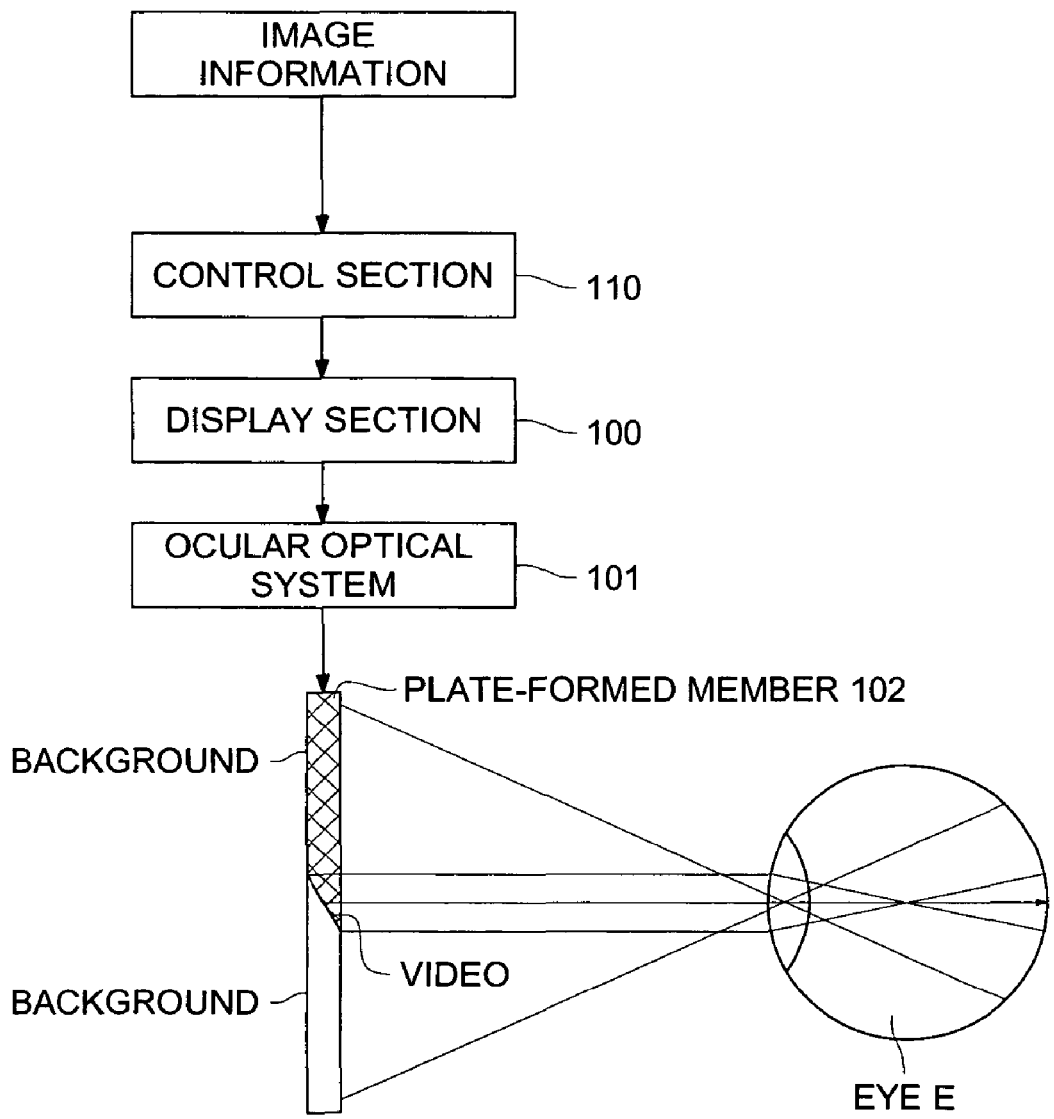
FIG. 15 is a configuration block diagram representing a transmission type video display apparatus as a first embodiment.
Figure 16:
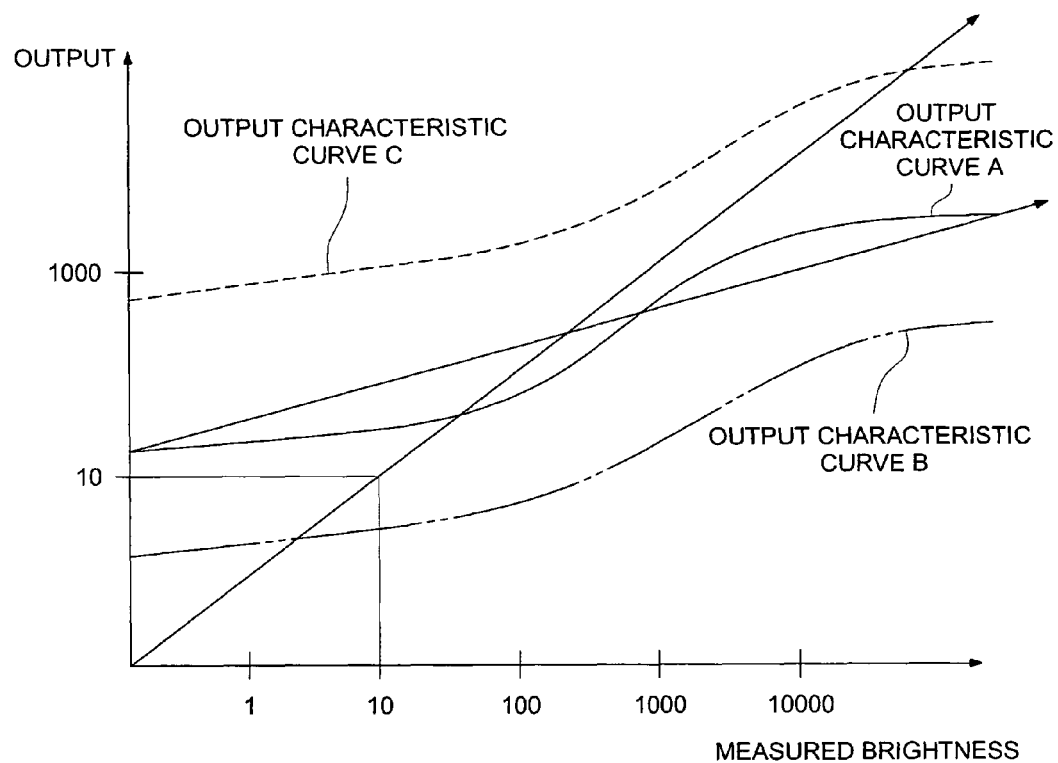
FIG. 16 is a diagram representing the characteristic curve of luminance ratio compression control.
Figure 17:
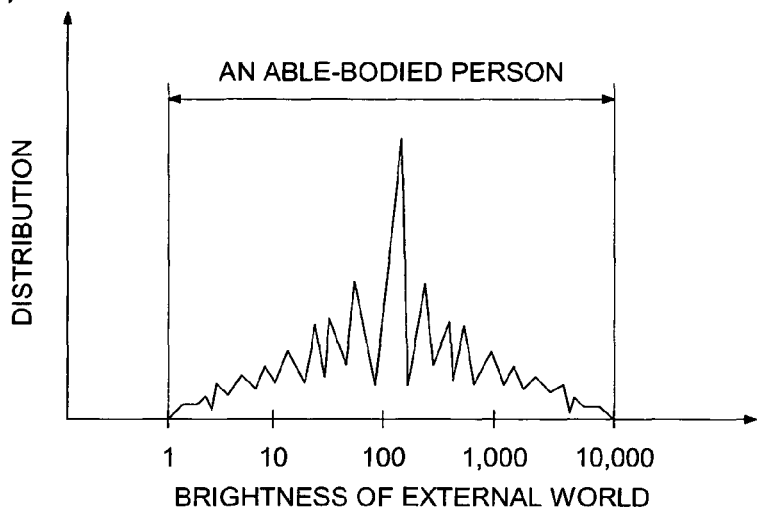
FIG. 17(a) is a drawing showing the luminance ratio compression control.
FIG. 17(b) is a drawing showing the luminance ratio compression control.
FIG. 17(c) is a drawing showing the luminance ratio compression control.
Figure 17:
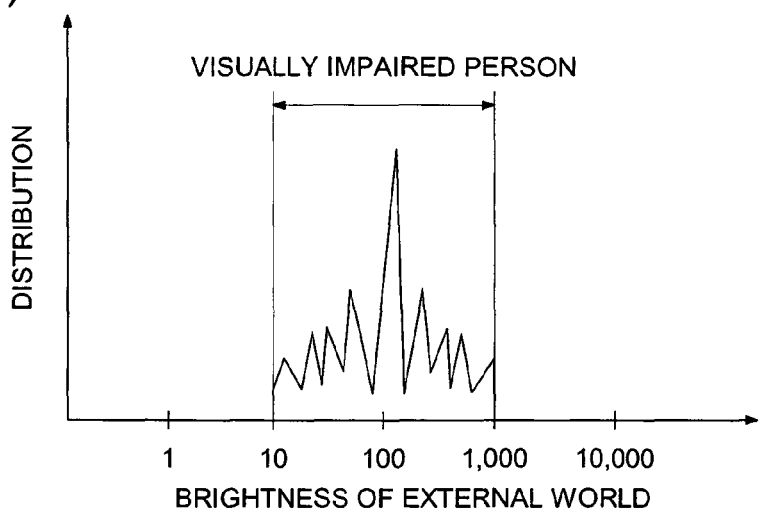
Figure 17:
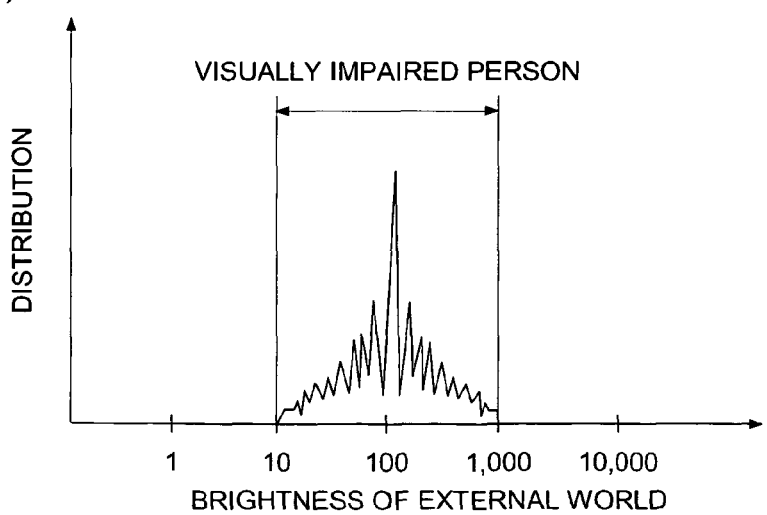

The visual aid display apparatus as a third embodiment of the present invention is configured as shown in FIGS. 15 through 17. FIG. 15 is a configuration block diagram representing video display apparatus. FIG. 16 is a diagram representing the characteristic curve of luminance ratio compression control. FIG. 17 is a drawing showing the luminance ratio compression.

The visual aid display apparatus 1 of the present embodiment comprises a display section 100 for displaying video, an ocular optical system 101, and a transparent plate-formed member 102 for holding the ocular optical system 101. The display section 100 is connected with the control section 110, and image information is inputted from the captured-image section and reproduction section to the control section 110. The display section 100 displays video under the control of the control section 110.

The light from the display section 100 is led into the eye E by the ocular optical system 101 to provide a virtual image of the video displayed on the display section 100 and to allow the light of the external world to pass through the plate-formed member 102, in such a way that the light is led to the eye E, whereby the outside image is provided.

In the present embodiment, the luminance ratio of the image information inputted by image processing under the control of the control section 110 is compressed and displayed on the display section 100. The luminance ratio compression control is provided on the basis of a lookup table as shown in FIG. 16. Control is made according to the output characteristic curve A so that the brightness shown on the display section 100 is kept within a predetermined range, with respect to the brightness of the image information. This output characteristic curve A is configured so as to give a greater output in the dark area and a smaller output in the light area. Depending on the degree of the disorder of a visually impaired user, this output characteristic curve A can be adjusted as shown in the output characteristic curve B or output characteristic curve C.

As shown in FIG. 17(a), the brightness that can be viewed by an able-bodied person ranges from 1 to 10,000 lx. The optimum range of illumination for a visually impaired user is much smaller than that of the able-bodied person and is from 10 through 1,000 lx, for example. Accordingly, as shown in FIG. 17(b), the level of light in the bright range of 1,000 lx or more, for example, is dazzling to the visually impaired user, and the that in the dark range of 10 lx, for example, is too dark for viewing. Thus, visibility deteriorates on two sides of the range of brightness. As described above, the visibility for the visually impaired user is reduced on both the dark and bright sides. As shown in FIG. 17(c), the luminance of the image information is compressed and an image is displayed on the display section 100. This arrangement provides the video comfortably viewable to the visually impaired user, without sacrificing the image information of a specific brightness, and avoids deterioration of visual acuity.

The control section 110 provides control in such a way that the brightness on the display section 100 does not exceed 1,000 cd/m$^2$. More comfortable, easy-to-see video can be ensured when the brightness on the display section 100 is kept below 1,000 cd/m$^2$. If the upper limit of the brightness is determined or the luminance ratio is compressed, the contrast will be reduced and a poor visibility will result. Accordingly, the control section 110 increases the chroma of the inputted image information, and gives a display on the display section 100, whereby comfortable video of high visibility is provided. Further, the control section 110 enhances the profile of the inputted image information before the image is displayed on the control section 110. This arrangement ensures comfortable video of higher visibility.

Embodiment

The luminance ratio of the inputted image information was compressed to 10 to 1, and the image was displayed on the visual aid display apparatus of the present invention. The apparatus was used by ten subjects aged between 60 and 75 for one hour. Before and after the use, visual acuity tests were conducted. For the nine subjects, no change in visual acuity was recorded. Only one person experienced deterioration of visual acuity from 0.7 to 0.5.

For comparison, the same tests were conducted without the luminance ratio of the inputted image information being compressed. No change in visual acuity was recorded for five persons, but five persons experienced deterioration of visual acuity.

Embodiment 4

Figure 18:
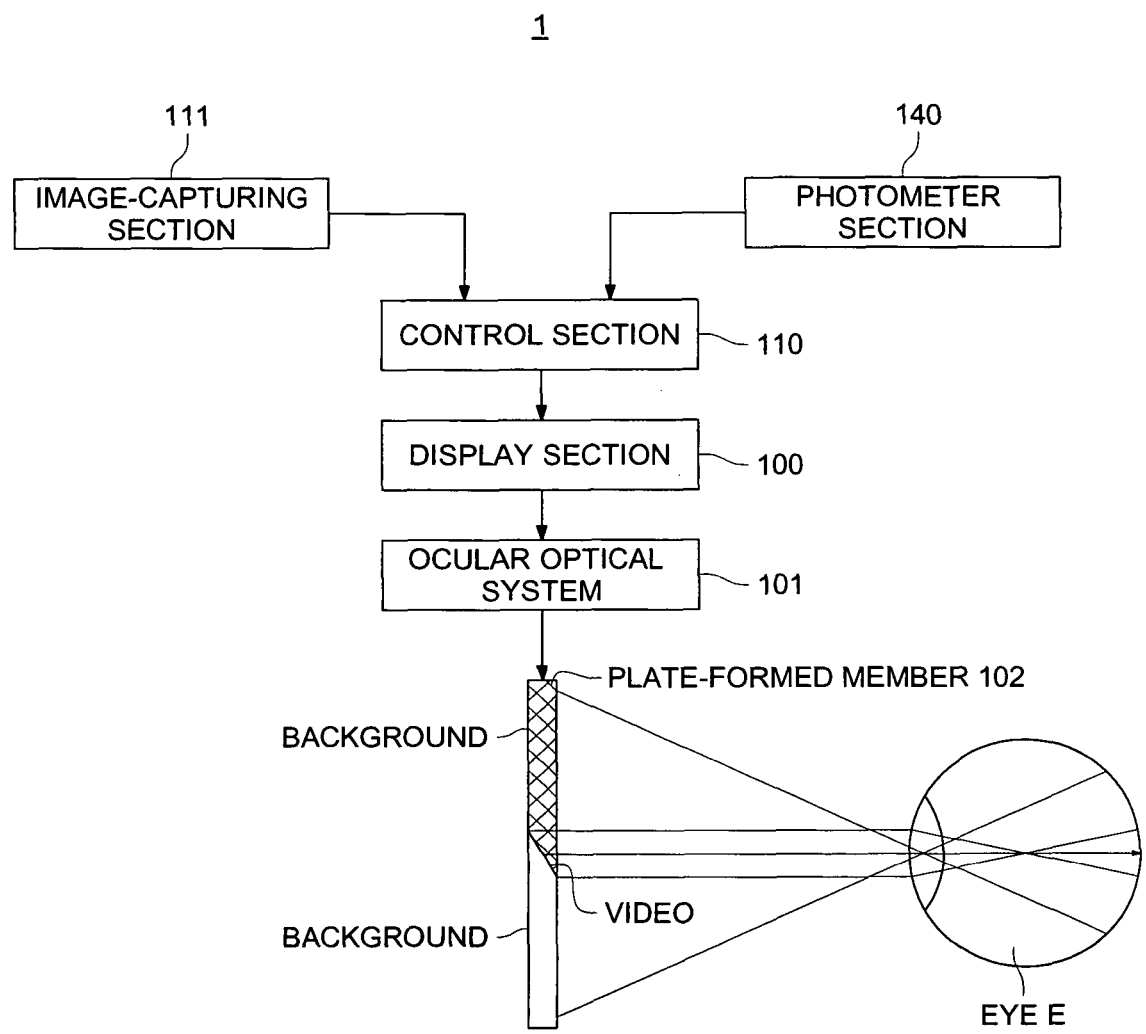
FIG. 18 is a configuration block diagram representing the transmission type video display apparatus as a third embodiment.
Figure 19:
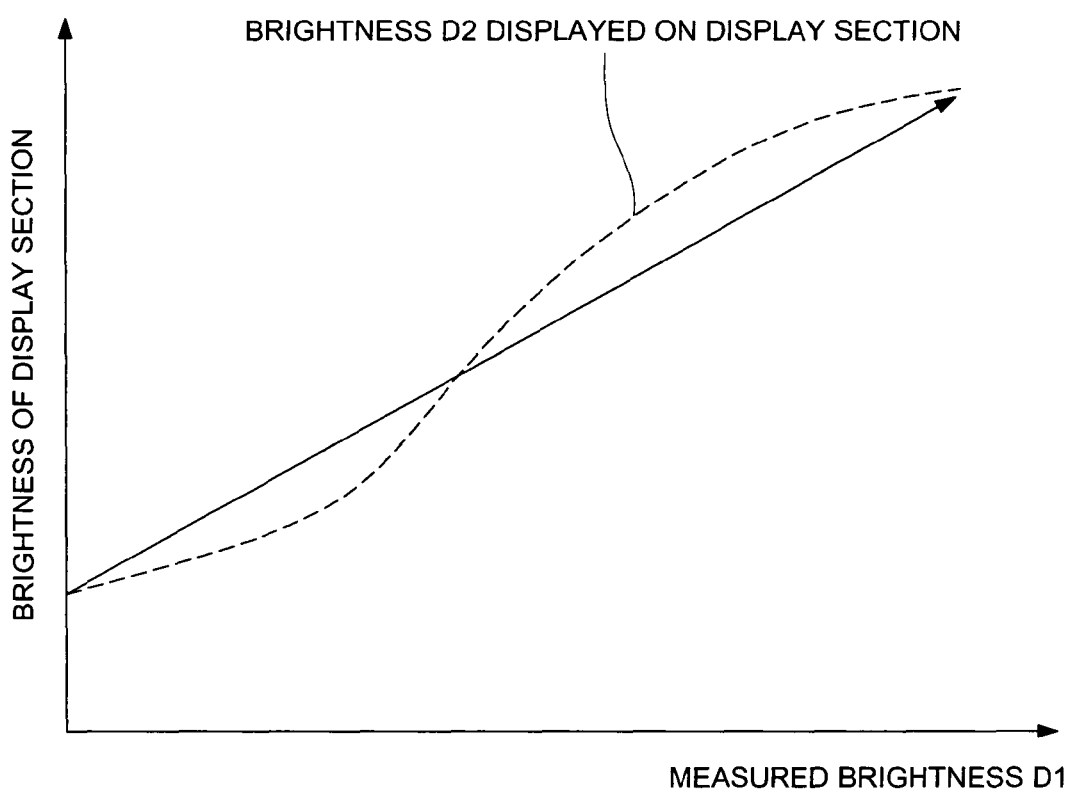
FIG. 19 is a diagram representing the characteristic curve of control in response to measured brightness.

The fourth embodiment of the visual aid display apparatus according to the present invention is configured as shown in FIG. 18. FIG. 18 is a configuration block diagram representing the visual aid display apparatus. FIG. 19 is a diagram representing the characteristic curve of control in response to measured brightness. The visual aid display apparatus 1 of the present embodiment has the same configuration as that shown in FIGS. 15 through 17. It is equipped with an image-capturing section 111 and photometer section 140. The video captured by the image-capturing section 111 is shown on the display section 100 by the control section 110. The light from the display section 100 is led to the eye E by means of the ocular optical system 101, whereby the virtual image of the video shown by the display section 100 is presented. At the same time, the light from external world is led to the eye E through the plate-formed member 102, whereby the image of the external world is presented. The control section 110 controls the brightness displayed on the display section 100 in response to the brightness measured by the photometer section 140. The image-capturing section 111 can be configured to fulfill the function of the photometer section 140.

The control conforming to the brightness measured by the control section 110 is provided according to the lookup table, as shown in FIG. 19. The control operation conforms to the output characteristic curve wherein the brightness D2 displayed in the display section 100 is increased in response to the measured brightness D1. As described above, visually impaired user is provided with the comfortable video of high visibility, with the surrounding brightness taken into account. Thus, the visual acuity of visually impaired user is not reduced. This output characteristic curve can be adjusted in conformity to the degree of disorder of the visually impaired user.

The brightness on the display section 100 is controlled not to exceed 1,000 $cd/m^2$. To ensure that the apparatus can be used more comfortably by the visually impaired user, the brightness on the display section 100 is preferred not to exceed 500 $cd/m^2$, and is more preferred not to exceed 300 $cd/m^2$.

The present invention is worn on the face of an observer, and the image information obtained by image-capturing operation is processed so that it can be displayed as video. Then the image information having been subjected to image processing is presented on the display area. This arrangement allows the video to be close to the one that can be viewed at normal times. Moreover, both the video of the external field and the image-processed image on the display area can be viewed by the observer on the display section. This allows an actual landscape to be identified, and permits the eyes of the observer to be confirmed by the person providing medical treatment. Further, when the apparatus is worn on the face of the visually impaired user suffering from cataract, glaucoma, macular degeneration or night blindness, a person talking face to face with him or her in the daily life can enjoy conversion by viewing his or her eyes. Thus, the present invention provides a visual aid display apparatus that can be used without giving a sense of incompatibility in the daily life.

The display area is set in such a way that the size in the longitudinal direction is greater than that in the lateral direction, and the display ratio is determined to provide portrait orientation. Thus, the display area configured in portrait orientation provides excellent visibility.

The display section installation site can be changed. It can be changed freely in response to the requirements of the observer.

The transmittance of the display area does not exceed 40% as compared to that around the display area. When no image is displayed, the display area works as a glass ball, and a doctor or the person sitting in front can watch the movement of the eyeballs of the observer.

The information required for display can be extracted from the image-capturing visual field of the image capturing section. Based on the image information, the size of the display area can be adjusted to assist the observer to get easy viewing.

Further, the information required for display can be extracted from the image-capturing visual field of the image capturing section. Based on the image information, the display area can be moved to assist the observer to get easy viewing.

Based on the image characteristic information obtained from the image capturing section, enlarged display is given, thereby assisting the observer to get easy viewing.

The present invention assists the observer to get easy viewing, by image processing such as enlargement/reduction processing, frequency correction, color tone correction and luminance compression.

Approach to a subject is detected and a warning is issued, whereby the observer is notified of a possible danger.

Further, the luminance ratio of the inputted image information is compressed, and the information is displayed on the display section. For example, when the apparatus is used as glasses for a visually impaired user, the apparatus easily provides comfortable, easy-to-see video, without sacrificing the image information in a specific wavelength area.

The luminance ratio of the image information inputted according to the image obtained by image-capturing operation of a subject is compressed and this information is displayed on the display section. This arrangement provides the visually impaired user with comfortable, easy-to-see video, without the image information in a specific wavelength area being sacrificed.

Control is provided in such a way that the brightness on the display section does not exceed 1,000 $cd/m^2$. This arrangement provides more comfortable, easy-to-see video.

The chroma of the inputted image information is increased and the information is displayed on the display section, whereby more comfortable, easy-to-see video is provided.

The profile of the inputted image information is enhanced before the image is displayed on the control section. This arrangement provides more comfortable, easy-to-see video.

The brightness of the image displayed on the display section is controlled in conformity to the brightness measured by the photometer section through image capturing of an object. This arrangement provides the visually impaired user with comfortable, easy-to-see video, with the surrounding brightness taken into account.

What is claimed is:

1. A visual aid display apparatus comprising:
   an image capturing section for capturing a subject;
   an image processing section for performing processing so as to display the image data obtained from the image capturing section;
   a display section further comprising:
   a display device for displaying the video of the image data processed by the image processing section, and
   an ocular optical system for providing video by leading the light from the display device to the eyes; and
   a control section for providing control in such a way that the video of the processed image can be displayed in display area of the display section;
   wherein the processing section performs processing for providing a visual aid display which is different from a current display and wherein the video of the external world and processed image in the display area are visible concurrently on the display section.

2. The visual aid display apparatus of claim 1, wherein the size of the display area setting the size in the vertical direction is greater than that in the lateral direction.

3. The visual aid display apparatus of claim 1, wherein an installation site of the display area can be changed.

4. The visual aid display apparatus of claim 1, wherein the transmittance in the display area does not exceed 40 percent that in the area surrounding the display area.

5. The visual aid display apparatus of claim 1, wherein the control section is the information required for display is extracted from the image capturing visual field of the capturing section, and the size of the display area is changed, based on the image data.

6. The visual aid display apparatus of claim 1, wherein the control section extracts the information required for display, from the image capturing visual field of the capturing section, and moves the display area, based on the visual field information.

7. The visual aid display apparatus of claim 1, wherein the control section allows an enlarged view to be displayed according to the image characteristic information obtained from the image capturing section.

8. The visual aid display apparatus of claim 1, wherein the image processing section perform image processing, including enlargement/reduction processing, frequency correction, color tone correction, luminance compression and image extraction.

9. The visual aid display apparatus of claim 1, further comprising:
   a warning section for detecting approach to the subject and issuing a warning.

10. The visual aid display apparatus of claim 1, further comprising:
    a luminance processing section for processing the brightness on the display section does not exceed $1{,}000\ cd/m^2$.

11. The visual aid display apparatus of claim 1, wherein the chroma of the inputted image data is increased to display an image on the display section.

12. The visual aid display apparatus of claim 1, wherein the profile of the inputted image data is enhanced to display an image on the display section.

13. The visual aid display apparatus of claim 1, wherein the brightness displayed on the display section is controlled in conformity to a photometer section and the brightness measured by the photometer section.

* * * * *